United States Patent
Shilian (10) Patent No.: US 10,251,795 B2
(45) Date of Patent: Apr. 9, 2019

(54) METHOD OF ENCLOSING A HYGIENE KIT

(71) Applicant: Neda Shilian, Roslyn Heights, NY (US)

(72) Inventor: Neda Shilian, Roslyn Heights, NY (US)

(*) Notice: Subject to any disclaimer, the term of this patent is extended or adjusted under 35 U.S.C. 154(b) by 0 days.

(21) Appl. No.: 15/613,609

(22) Filed: Jun. 5, 2017

(65) Prior Publication Data

US 2018/0344543 A1 Dec. 6, 2018

(51) Int. Cl.
| | |
|---|---|
| *A61F 13/15* | (2006.01) |
| *A61F 13/551* | (2006.01) |
| *A61F 13/47* | (2006.01) |
| *A61F 13/58* | (2006.01) |
| *B65D 71/12* | (2006.01) |

(52) U.S. Cl.
CPC .......... *A61F 13/5519* (2013.01); *A61F 13/47* (2013.01); *A61F 13/5514* (2013.01); *A61F 13/58* (2013.01); *B65D 71/12* (2013.01); *A61F 2013/4708* (2013.01); *A61F 2013/582* (2013.01)

(58) Field of Classification Search
CPC ...... B65D 71/12; A61F 13/5519; A61F 13/47; A61F 13/5514; A61F 13/58; A61F 13/55145; A61F 2013/55145; A61F 2013/4708; A61F 2013/55195; A61F 13/5513; A45C 5/005
USPC ............................ 206/581; 604/385.06, 358
See application file for complete search history.

(56) References Cited

U.S. PATENT DOCUMENTS

| | | | | |
|---|---|---|---|---|
| 4,383,327 A * | 5/1983 | Kruger | ..................... | A61B 6/06 378/146 |
| 4,948,267 A * | 8/1990 | Kaldenbaugh | ......... | B65D 33/01 206/278 |
| 5,261,531 A * | 11/1993 | Nieves | ................ | A61F 13/5519 206/205 |
| 5,569,230 A * | 10/1996 | Fisher | ............... | A61F 13/47218 206/438 |
| 5,579,616 A * | 12/1996 | Farag | ........................ | E04B 2/96 52/204.5 |
| 5,893,459 A * | 4/1999 | Croft | ....................... | B65B 11/50 206/460 |
| 6,350,931 B1 * | 2/2002 | Martin | ............. | A61F 13/55175 206/225 |
| 7,104,977 B2 * | 9/2006 | Price | ........................ | A41B 9/00 206/581 |
| 7,144,391 B1 * | 12/2006 | Kreutz | ................. | A61F 13/2051 604/385.17 |
| 7,942,857 B2 * | 5/2011 | Chicoine | ............. | A61F 13/5514 206/440 |
| 8,141,711 B2 * | 3/2012 | Perry | ................ | A61F 13/55175 206/440 |
| 8,991,610 B2 * | 3/2015 | Kuroda | ............... | A61F 13/5514 206/38 |
| 9,375,366 B1 * | 6/2016 | Morisi | ................ | A61F 13/5519 |
| 2003/0136704 A1 * | 7/2003 | Burgess | ............. | A61F 13/5519 206/581 |
| 2004/0191315 A1 * | 9/2004 | Slattery | .................. | A01N 25/34 424/486 |
| 2008/0083774 A1 * | 4/2008 | Sawin | ................ | B65D 77/0453 221/190 |
| 2010/0078351 A1 * | 4/2010 | Sherrill | ................. | A61F 13/551 206/570 |

(Continued)

*Primary Examiner* — Steven A. Reynolds (57) ABSTRACT

A hygiene kit containing a set of hygiene products folded, arranged, compressed, and packaged into a pocket-sized container.

5 Claims, 9 Drawing Sheets

(56) References Cited

U.S. PATENT DOCUMENTS

| | | | |
|---|---|---|---|
| 2013/0206640 A1* | 8/2013 | Mann, Jr. | A45C 11/008 206/581 |
| 2015/0090629 A1* | 4/2015 | Diaz-Santiago | A61F 13/5519 206/581 |
| 2015/0265523 A1* | 9/2015 | Ueda | A61K 8/41 424/401 |
| 2016/0107822 A1* | 4/2016 | Maalouf | B65D 83/0888 206/449 |

\* cited by examiner

METHOD OF ENCLOSING A HYGIENE KIT

BACKGROUND

Maintaining feminine hygiene is very important to a women's overall health, in addition to preventing odors, itching, and discomfort, practicing feminine hygiene can prevent bacterial infections from occurring. In some cases, bacterial infections may lead to sterility, disease, cancer, and other health problems. To maintain feminine hygiene, it is necessary to bathe regularly, develop healthy habits in regards to the menstrual cycle, and wear fabrics that allow the vaginal region to breathe. Underwear, panty liners and feminine wipes are commonly sold in the retail stores in a variety of different styles and packaging.

Women popularly use personal care articles such as an underwear, panty liners and wipes. One reasons women choose to wear underwear is to help them feel comfortable and confident. It also plays an important role in hygiene protecting the vaginal area from infections and parasites such as crabs and public lice. It helps prevent minor rashes that can happen when delicate skin in the private areas chafes against the pants. It protects clothing from stain due to discharges, lubrication, menstrual blood, fecal matter, urine, or other substances. The genital area has a higher risk of attracting harmful bacteria than the majority of other regions of the body, making it necessary to change underwear frequently.

Absorbent articles such as a panty liner are intended to absorb sweat, vaginal fluids and other vaginal discharges from the uterus. Wipes come in the forms of wet or dry. Women purchase these items in large quantity packaging as they rely strongly on maintaining proper hygiene and feeling clean throughout their day. Most women change their underwear at least once a day, wear panty liners regularly, and use feminine wipes to manage vaginal discharge, odors, sweats, and anything else that is unpleasant.

For many women this is a lot more common during their primarily mid-cycle (during ovulation) to manage their increased vaginal discharge. Moms of new babies also tend to have light postpartum vaginal flow a few weeks after giving birth as well and experience uncomfortable discharges. Slight vaginal discharge is very common and can be extremely frustrating. Some women may accidentally wet their pants after having a good laughing session. Panty liners are a commonly used and are a popular option for controlling and managing vaginal discharges. Many woman routinely stash individually wrapped panty liners, tampons, and wipes randomly in their purses along with all their other routinely carried items such as the makeup bag, phone, keys, etc.

Women purchase individually wrapped panty liners and individually wrapped feminine wipes separately in bulk packaging that contain 20+ units per box. These items are sold in large quantity boxes and each comes as a separate product for purchase. Women may take the desired quantity of the individually wrapped liner or wipes out of the multi-pack box and place them in their purses. However, this requires women to keep track of panty liners and feminine wipes, and in the event of accidental discharge, an additional pair of underwear. Additionally, women must carry purses to carry these items.

Many women wash their Undergarments before an initial wear due to concerns about cleanliness and safety. The underwear may have fallen on the factory floor, or other people may have handled or even worn the underwear. Germs such as staphylococcus, MRSA and norovirus may be found on even new underwear under those conditions. Also, new underwear may have residual chemical leftovers from the manufacturing process. These chemicals often cause irritation or an allergic reaction.

What is needed is a compact women's hygiene kit containing individually wrapped items that fits conveniently in a woman's purse, pocket, or hand.

SUMMARY

This application contemplates a hygiene kit containing a set of hygiene products folded, arranged, compressed, and packaged into a small, hand-held, pocket-sized container. The hygiene kit may include a pair of underwear, a panty liner, a wipe, and a wash-me-bag. The underwear, panty liner, and wipe may be enclosed in the wash-me-bag and the wash-me-bag may be enclosed in a small container or box. Alternatively, the underwear, panty liner, wipe, and wash-me-bag may be folded or otherwise disposed in the container. The underwear, panty liner, and wipe may be placed in a pile, the pile having a thickness, a width, and a length. The underwear, panty liner, and wipe are each folded so that when they are stacked together, their measurements do not exceed the measurements of the pile. Ideally, the pile is between 1.5 and 3.7 inches in width, 1.5 and 3.7 inches in length, and 0.19 and 1 inches in thickness. In one embodiment, the items are stacked vertically or horizontally in the pile. In another embodiment, the items are stacked side by side. In a third embodiment, items are stack both side by side and in piles. The pile may include the wash-me-bag as a separate item folded and added unto it, with the entire pile placed into a container. One or more items, such as the underwear, liner, and wipe, may be added into the wash-me-bag, and the pile, which may include the wash-me-bag, may be disposed in a container.

The wipe and panty liner may each be placed in individual wrappers. The wrappers may be made of plastic, foil, or any suitable material. The underwear may be folded and disposed between the wipe and panty liner in the pile. Alternatively, the wipe or panty liner may be placed in the middle. Ideally, the wipe and the panty liner are each stiffer than the underwear, thereby providing structural support to the pile.

The wipe is ideally PH Balanced, hypoallergenic, free from chlorine, alcohol, dyes, paraben, and phthalate. It may comprise a non-woven cloth folded within a fully sealed foil wrapper. The wrapper may be notched for easier unsealing by a user. It may be flushable or designed to be thrown away. The wrapper may feature a corporate or product logo matching the a corporate or product logo featured on the panty liner, the underwear, the wash-me-bag, and the container. The wipe wrapper may measure between 1.5 and 3 inches in width and 1.5 and 3 inches in length and the wipe itself may measure, once unfolded, approximately between 3 to 10 inches in width and 3 to 10 inches in length, with a thickness less than 1/32 inches. The wipe is designed to gently clean intimate areas of the body and then to be disposed. The wipe may be scented.

The panty liner may be configured to be placed on the inside crotch of the underwear. The panty liner may be disposed flush against a panty liner wrapper, and then folded in conjunction with the wrapper until a first end of the wrapper passes over a second end of the wrapper. The first end may attach to the second end by means of a sticker or other adhesive. A corporate or product logo may be placed on the sticker or on the wrapper itself. Ideally, the wrapper features a first and second perimeter portion, with a first end of the first perimeter portion sealed to a second end of the first perimeter portion and a first end of the second perimeter portion sealed to a second end of the second perimeter portion. The wrapper, when folded in conjunction with the panty liner, may measure between 3 and 3.5 inches in width, between 2 and 2.5 inches in length, and approximately ⅛ inch in thickness. In a broader embodiment, the folded wrapper and panty liner measure 1.5 to 3.75 inches wide and 1.5 to 3.75 inches long. In another embodiment, the thickness is 0.04 to 0.08 inches. When unfolded, the wrapper may measure approximately 5 to 7 inches in length, between 2 and 2.5 inches in width, and less than 0.04 inches in thickness. The panty liner may comprise a first non-permeable outer layer, a second non-permeable outer layer, a first absorbent inner layer, and a second absorbent inner layer. The liner may measure 5 to 6.5 inches in length, 1.5 to 2.5 inches in width, and less than 0.04 inches in thickness. The first non-permeable outer layer may be flush against and removably attached to the first absorbent inner layer by means of a glue or adhesive alternative, such as a sticky plastic layer. The first absorbent layer may be more absorbent than the second absorbent layer. In one embodiment, the wrapper may measure between 2 and 3.5 inches in width, 2 and 3.5 inches in length, and 0.10-0.30 cm in thickness. In one embodiment, the panty liner wrapper, when unfolded, may measure between 2 and 3.5 inches in width and 5.5 and 7 inches in length. The panty liner may measure between 5 and 6.5 inches in length, 1.65 and 2.5 inches in width, and less than 1 mm in thickness.

The panty liner may be configured to be placed on the inside crotch of the underwear, to decrease the contact between the user's intimate parts and the underwear, which may or may not be washed. The crotch protector panty liner will provide conformability to fit both thong and bikini underwears. It feature a top surfaced designed to be non-irritable to skin, specifically membranous or intimate skin. The top sheet layer of the panty crotch liner may be constructed of any material and may be designed to retain very little liquid by limiting thickness to less than 1 mm; in this version, it may not be suitable for heavy bodily fluids such as menstrual fluid. Additionally the crotch panty liner can include any desired pattern or array of embossments on the body side surface or the article. The desired arrangements may include an absorbent body structure that has embossment regions formed on at least one surface. The other components of the article may also include corresponding embossed regions.

The underwear may be a thong or bikini-type bottom. The underwear may be soft, and stretchy, made from any suitable material such as spandex, nylon, cotton, woven fabric, a knitted fabric, a nonwoven fabric or the like, as well as combinations thereof. It may be disposable or designed to be reusable after washing.

The underwear may be folded first along the longest dimension until it forms a strap 1.50-2.25 inches wide. This strap can then be folded on both sides toward the center in a series of folds, each fold also measuring between 1.50 and 2.25 inches, until the folds on either side are disposed in a layer between 0.20 and 1 inch. In one embodiment, the strap folds may measure between 1 and 3 inches in width, and the underwear, when folded, may measure between 0.20 and 1 inch thick. In a narrower embodiment, the folded underwear measures between 0.2 and 0.5 inches thick.

The reusable underwear may be rolled, folded, otherwise reduced in size in any operative manner or configuration when the pile is assembled into the wash me bag, assembled within the wash-me bag and placed inside a container, or placed directly in the container.

The wash-me-bag may be configured to store and compress the pile. It may also be configured to receive laundry such as a used soiled underwear. The wash-me-bag may feature printed graphics and comprise a first end and a second end. It may be made of plastic, paper, pvc, foil, or similar materials. The first end may include an opening in which the pile may be inserted and removed, with an attachment mechanism such as glue or glue-alternative applied to an enclosure tab extending from the first end. The enclosure tab is configured to removably attach to an enclosure end situated on the second end. Between the first end and the second end may be a sleeve portion, with the sleeve portion being continuous with the first end and the second end. The sleeve portion may feature two layers of material, each layer connected to the other layer at a peripheral edge. The wash-me-bag in an unfolded state may measure between 2.3 and 4.7 inches wide and 2.4 and 7.9 inches long.

The pile may be compressed before being placed in the wash-me-bag. This compression may include compressing the width of the pile as well as the thickness. The pile may first be passed through the opening and then pushed or otherwise eased toward the second end. In one version, it is pushed through the opening but not eased past the first end toward the second end. The first end may then be folded over a first side of the second end until the enclosure tab wraps around the second end and attaches to the enclosure end situated on the second side of the second end. Attaching the enclosure tab to the enclosure end may further compress the thickness of the pile where it is disposed inside the wash-me-bag as well as the length of the pile, which previously may or may not have been compressed.

In one embodiment, the pile is not placed inside the wash-me bag, but adjacent to it, both disposed within a container. In this embodiment, the wash-me-bag may be folded in conjunction with the other elements in the pile or may be folded separately and added to the pile. In another embodiment, the pile includes the wash-me-bag, which is then placed in the container. The container may be made of cardboard, paper, pvc, fabric, plastic, or metal. In the plastic variant, the container may be transparent. The container may close by means of a flap, a zipper, hinge, pivot-point, removable lid, bendable lid, sliding lid, adhesive such as glue or tape, or snap-fit button. The closure means may be configured to be re-closable after opening. The closure means may be configured to open hingedly, via a front or side portion of the container. The container and/or wash-me-bag may feature a hook for easier placement in stores.

The container may have one or more compartments for receiving the pile or elements thereof, and may in particular include a separate compartment for used elements, such as items to be laundered, discarded, or flushed. The compartments may be placed in series or in parallel, and adjacent to or coterminous with a main compartment. The container can include one or more separately provided components and may comprise a composite member that is integrally formed with a selected portion of a component or member of one or more of the employed pile items in the kit.

In one embodiment, the dimensions of the container are no greater than 3.7 inches in width and height. In another embodiment, the dimensions of the container are at least 1.5 inches in width and height. In one variation, the container is at least 0.2 inches but no more than 1.2 inches in thickness. In another embodiment, the container, with contents, may measure between 0.1 and 1 inch in thickness, 0.8 and 4 inches in length, and 0.8 and 4 inches in width.

In one embodiment, the dimensions of the container or wash-me-bag with the pile inserted into it are ratios of the average female palm size and length. That is, the ratio between the width of the container or wash-me-bag and the width of the palm may be 1:1, between 0.8:1 and 1:1, or between 0.5:1 and 0.8:1. The ratio between the length of the container or wash-me-bag in its folded state may be between half and equal to the previous ratio. The average female palm size is 2.9 inches wide and 6.8 inches.

BRIEF DESCRIPTION OF THE DRAWINGS

FIG. 8c shows an alternative embodiment of the container in FIG. 8a.

DETAILED DESCRIPTION OF THE DRAWINGS

Figure 1:
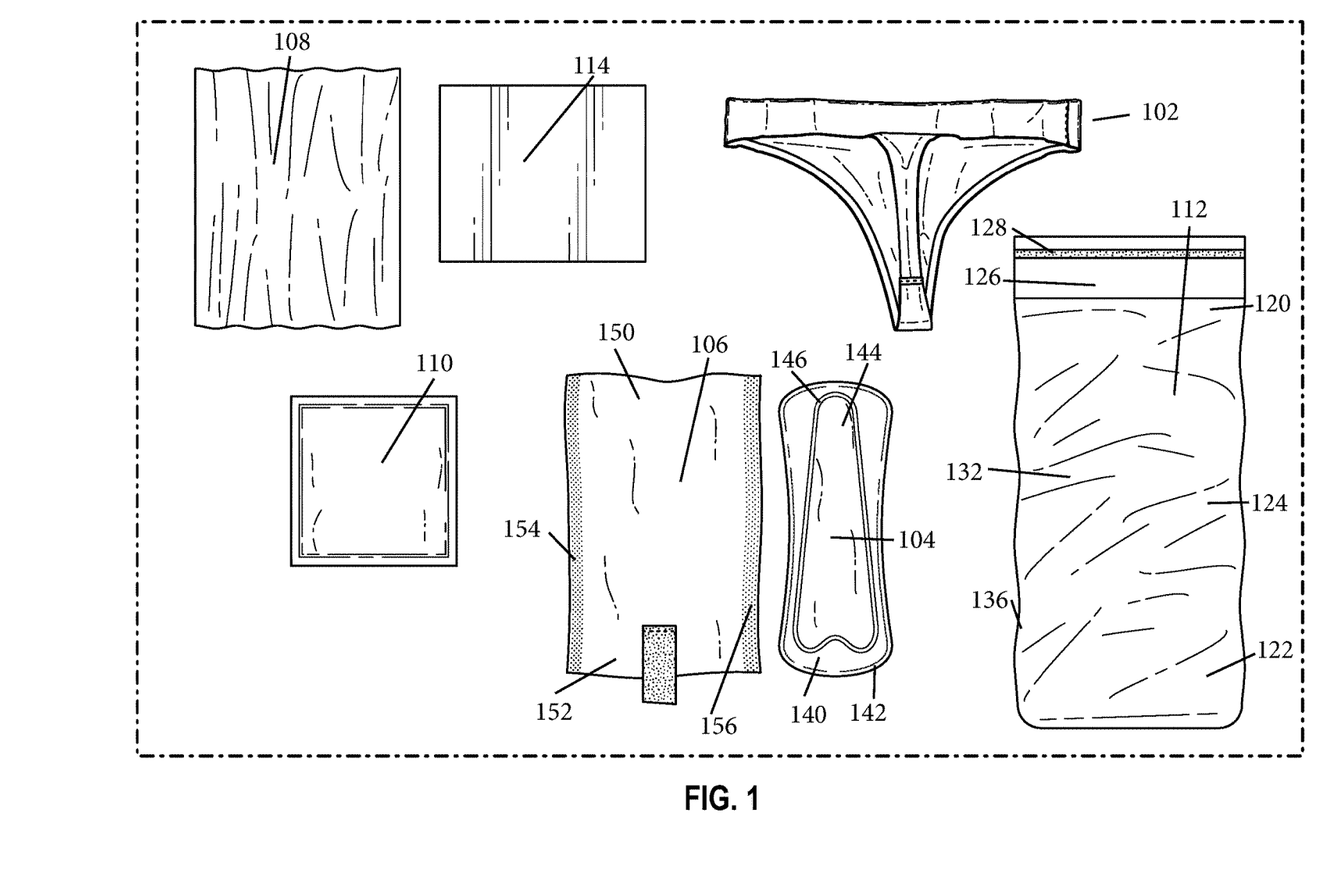
FIG. 1 shows an underwear, a panty liner, a panty liner wrapper, a wipe, a wipe wrapper, a wash-me-bag, and a box.
Figure 2A:
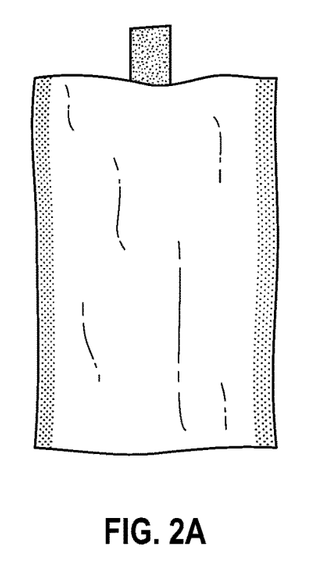
FIGS. 2a-d show the steps of folding a panty liner wrapper.
Figure 2B:
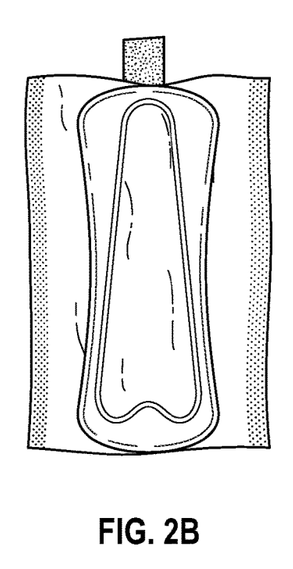
Figure 2C:
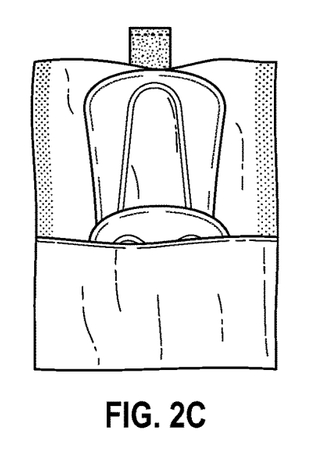
Figure 2D:
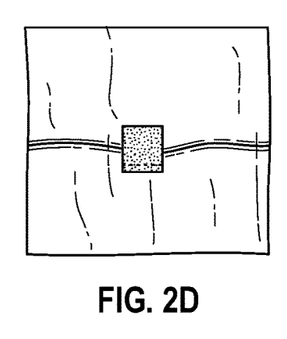

FIG. 1 shows an underwear 102, a panty liner 104, a panty liner wrapper 106, a wipe 108, a wipe wrapper 110, a wash-me-bag 112, and a box 114. Each of these items may have a logo.

The wash-me-bag has a first end 120, a second end 122, a sleeve portion 124. The first end has an opening 126 and an enclosure tab 128. The second end has an enclosure end 402 (see FIG. 4b). The sleeve portion has a first side 132 and a second side 404. The first side and second side are attached at peripheral edges 136.

The panty liner has a first non-permeable outer layer 140, a second non-permeable outer layer 142, which is opposite the first non-permeable outer layer, a first absorbent inner layer 144, and a second absorbent inner layer 146.

The panty liner wrapper has a first end 150, and a second end 152, a first perimeter portion 154, and a second perimeter portion 156.

As shown in FIGS. 2a-2d, the panty liner is wrapped in the wrapper by placing it flush against the wrapper, then folding the second end toward a center of the panty liner wrapper, then folding the first end over the second end and attaching the first end to the second end by an adhesive. The perimeter portions may then be sealed.

Figure 3A:
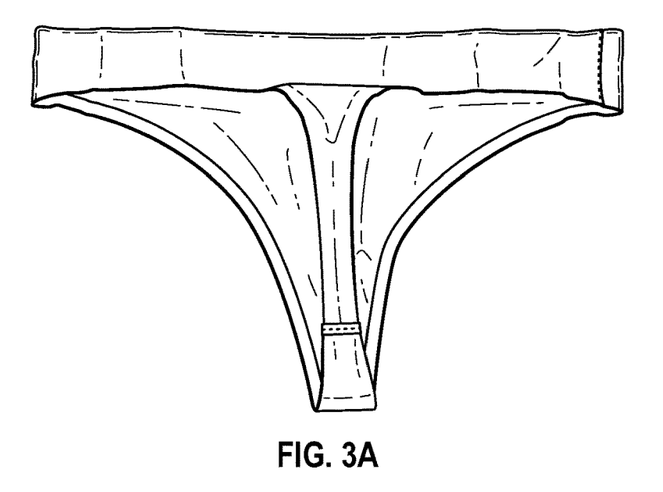
FIGS. 3a-c show the steps of folding underwear.
Figure 3B:
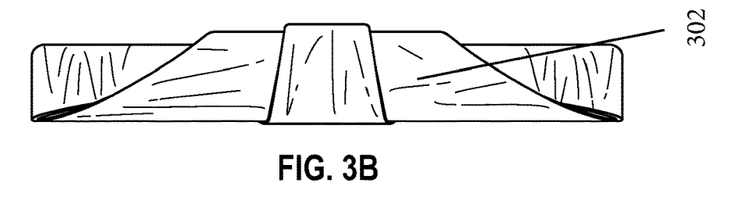
Figure 3C:
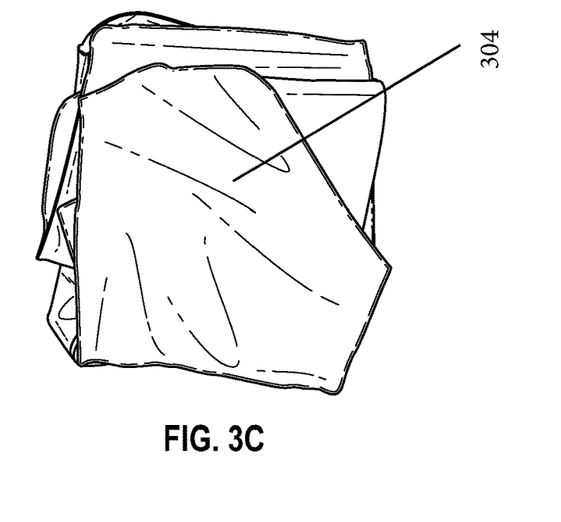

As shown in FIG. 3a-c, the underwear is folded along a first axis 302, and then folded along a second axis 304.

Figure 4A:
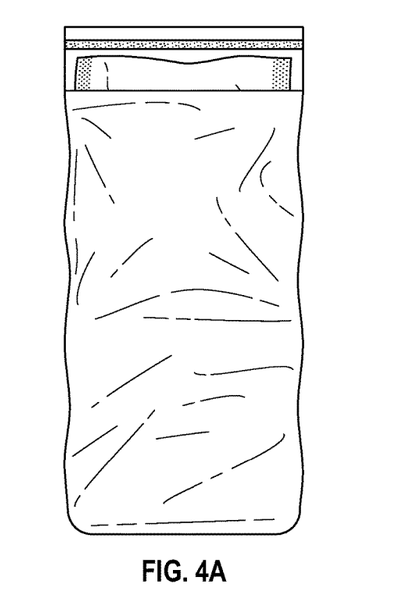
FIGS. 4a-c show the steps of inserting a pile and folding a wash-me-bag.
Figure 4B:
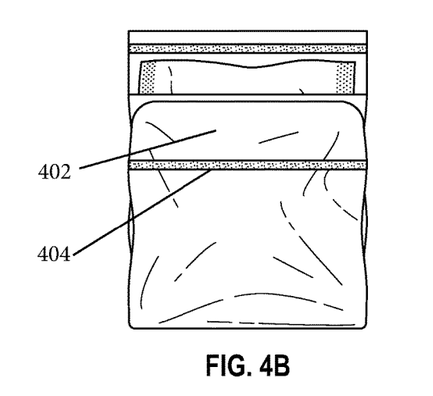
Figure 4C:
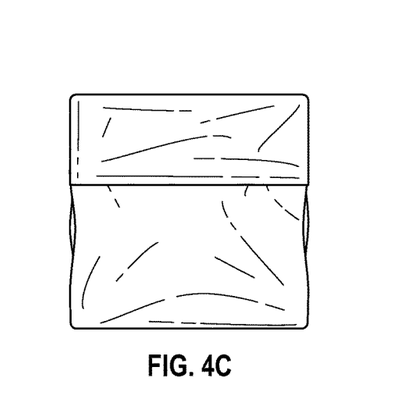

As shown in FIG. 4a-c, the pile is inserted into the wash-me-bag, the first end is folded over the second end, the enclosure tab is wrapped over and attached to the enclosure end 404 on the second side 402.

Figure 5A:
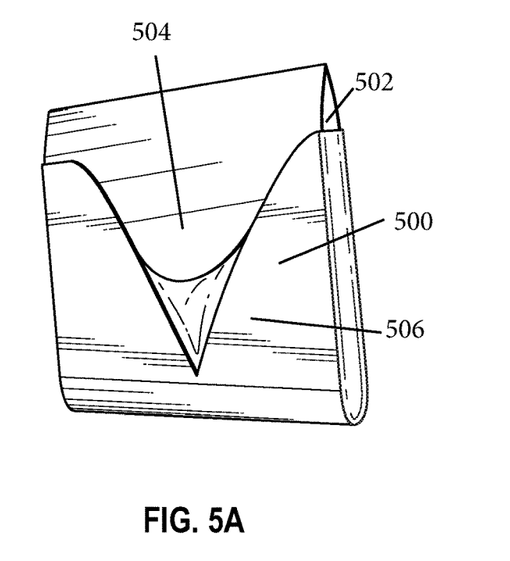
FIGS. 5a-b show an embodiment of a container.
Figure 5B:
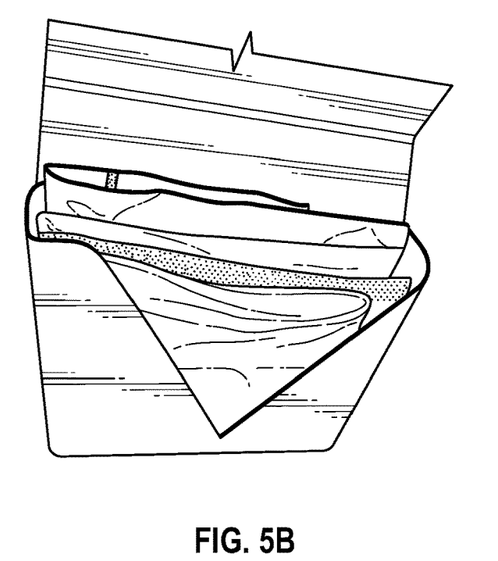

As show in FIGS. 5a-b, the pile is inserted into through the top side 502 of a flap container 500 with a flap 504 opening attached to the top side and pulled over and tucked under a front side 506.

Figure 6A:
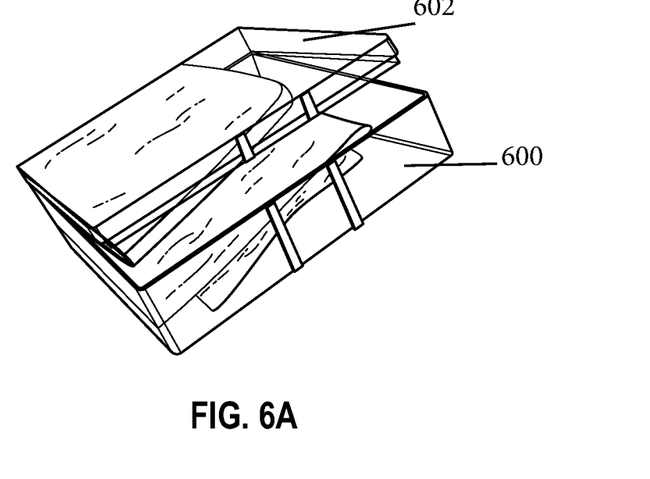
FIGS. 6a-b show an embodiment of a container.
Figure 6B:
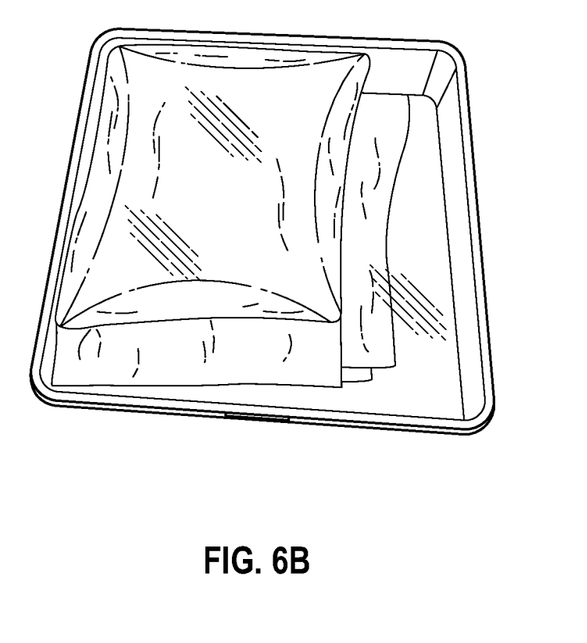

As shown in FIGS. 6a-b, the pile is inserted into a see-through container 600 with a lid 602.

Figure 7A:
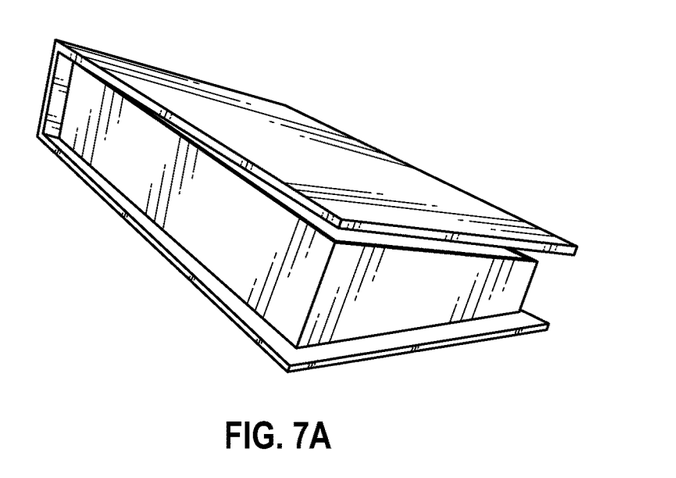
FIGS. 7a-b show an embodiment of a container.
Figure 7B:
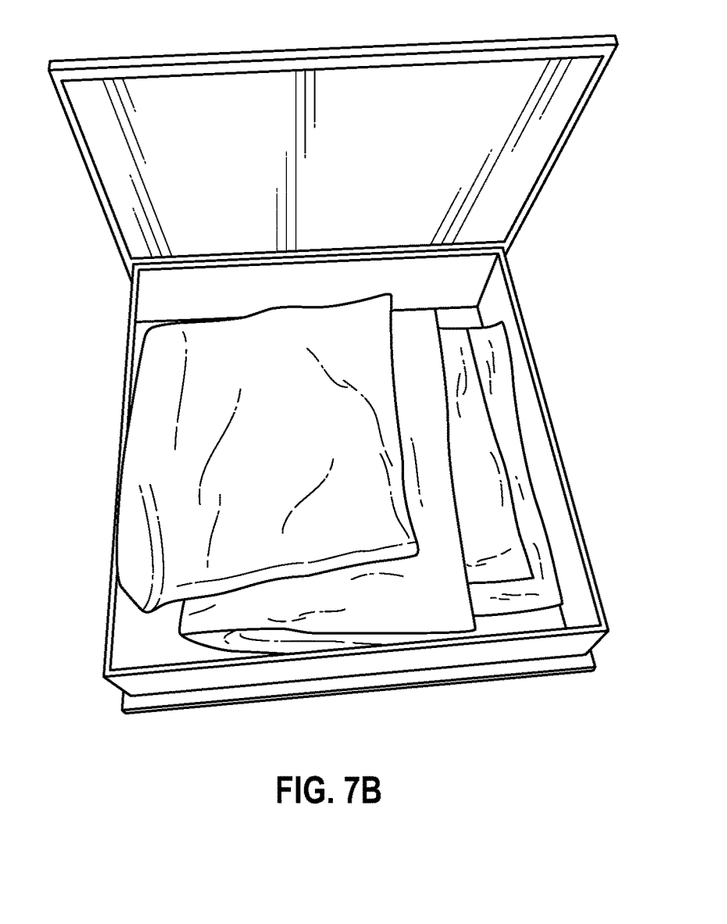

As shown in FIGS. 7a-b, the pile is inserted into a hinged container.

Figure 8A:
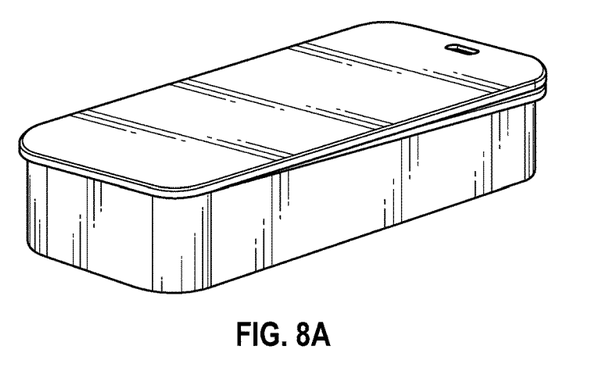
FIGS. 8a-b show an embodiment of a container.
Figure 8B:
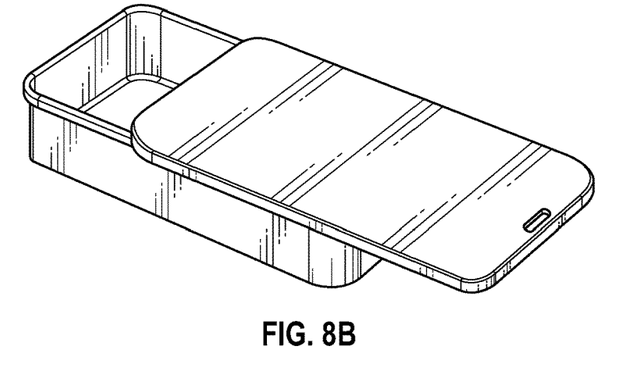
Figure 8C:
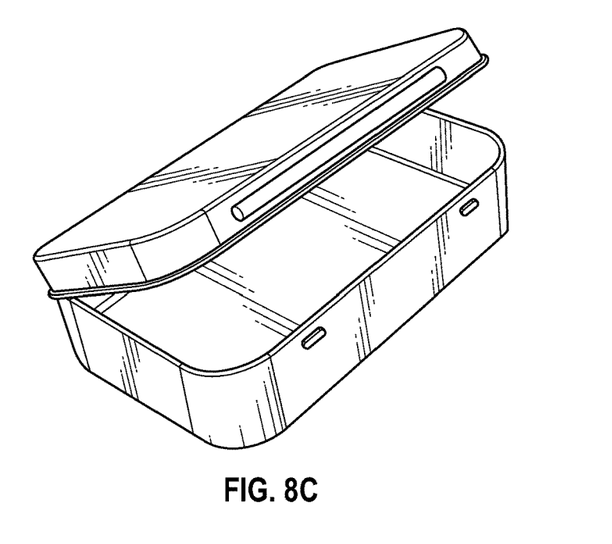

As shown in FIGS. 8a-c, the pile is inserted into a lidded container that ay slide open, as in FIG. 8b, or open hingedly, as in FIG. 8c.

Figure 9A:
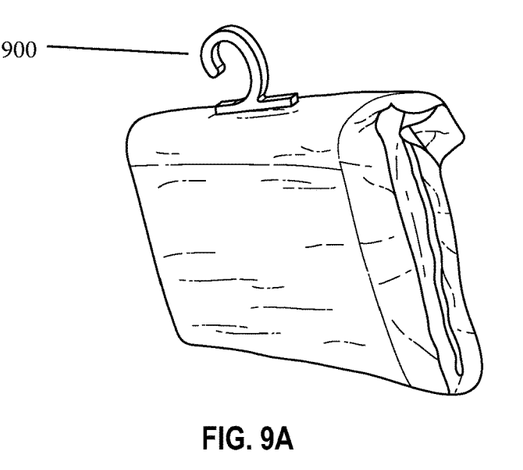
FIGS. 9a-c show hanger attachments for the containers in FIGS. 5a-c, 6a-c, and 7a-c.
Figure 9B:
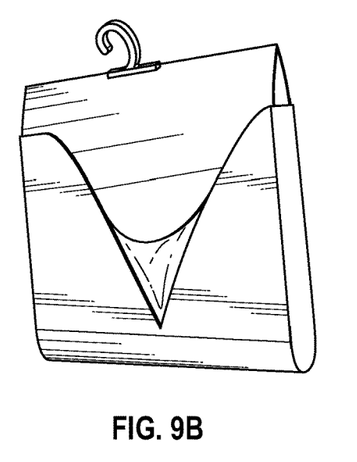
Figure 9C:
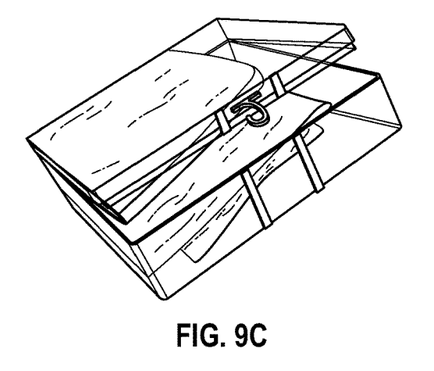

As shown in FIG. 9a, a hanger 900 may be attached to the wash-me-bag. As shown in FIG. 9b, the hanger may be attached to the flap of the flap container. As shown in FIG. 9c, the hanger may be attached to the lid of the see-through container. It is conceivable that the hanger may be attached do other parts of each container as well.

The invention claimed is:

1. A hygiene kit comprising underwear, a panty liner, a wipe, a wash-me-bag, and a container,
   a. the underwear, panty liner, and wipe arranged in a pile, the pile enclosed in the wash-me-bag, the wash-me-bag enclosed in the container, wherein the wash-me-bag is a bag for containing objects to be washed;
   b. the pile having a width between 0.85 and 4 inches, a length between 0.85 and 4 inches, and a thickness between 0.1 and 1 inch;
   c. the wipe comprising a non-woven cloth and a wipe wrapper;
   d. the non-woven cloth being folded and sealed within the wipe wrapper;
   e. the panty liner disposed flush against a panty liner wrapper and folded in conjunction with the panty liner wrapper, the panty liner and panty liner wrapper measuring between 1.5 and 3.75 inches in width, 1.5 and 3.75 inches in length, and between 0.04 and 0.08 inches in thickness when folded;
   f. the panty liner when unfolded measuring between 5 and 6.5 inches in length, 1.5 and 2.5 inches in width, and between 0.2 and 0.4 inches in thickness;
   g. the panty liner wrapper when unfolded measuring between 2 and 3.75 inches in width, 5.5 and 7 inches in length, and 0.02 and 0.04 inches in thickness;
   h. the underwear being folded along a first axis so that it forms a strap 0.8 to 3.5 inches wide and folded along a second axis towards a center of the strap, each fold along the second axis measuring between 0.8 and 3.5 inches, so that the underwear in a fully folded configuration measures between 0.8 and 3.5 inches in length, 0.8 and 3.5 inches in width, 0.1 and 1 inch in thickness; and
   i. the wash-me-bag comprising a first end, a second end, and a sleeve portion, the sleeve portion disposed between and being continuous with the first end and the second end, the first end including an opening and an enclosure tab, the second end including an enclosure end, the enclosure tab configured to removably attach to the enclosure end, the sleeve portion featuring a first side and a second side, the first and second sides attached at peripheral edges, the first end being folded over the first side of the second end, the enclosure tab wrapped around the second end and attached to the enclosure end.

2. The hygiene kit in claim 1, the wipe being PH balanced, hypoallergenic, and free from chlorine, alcohol, dyes, paraben, and phthalate, and the wipe wrapper being made of foil;
   a. the non-woven cloth and wipe wrapper being between 1.5 and 3 inches in width, 1.5 and 3 inches in length when folded together;
   b. the non-woven cloth, when unfolded, measuring between 3 and 10 inches in width, 3 and 10 inches in length, and less than 0.03 inches in thickness.

3. The hygiene kit in claim 1, the panty liner comprising a first non-permeable outer layer, a second non-permeable outer layer, a first absorbent inner layer, and a second absorbent inner layer, the first non-permeable outer layer being flush against and removably and adhesively attached to the first absorbent inner layer, the first absorbent layer being more absorbent than the second absorbent layer.

4. The hygiene kit in claim 3, the panty liner wrapper comprising a first end, a second end, a first perimeter portion, and a second perimeter portion, the first end attached to the second end by an adhesive, a first end of the first perimeter portion attached to a second end of the first perimeter portion, a first end of the second perimeter portion attached to a second end of the second perimeter portion.

5. The hygiene kit in claim 1, the underwear disposed between the panty liner and the wipe in the pile, and wherein the wipe wrapper with the wipe wrapper inside and panty liner wrapper with the panty liner inside each being stiffer than the underwear.

\* \* \* \* \*